United States Patent [19]

Galbo et al.

[11] Patent Number: 5,021,481

[45] Date of Patent: Jun. 4, 1991

[54] N-HYDROCARBYLOXY HINDERED AMINE LIGHT STABILIZERS WITH PHOSPHORUS MOIETIES

[75] Inventors: James P. Galbo, Hartsdale; Raymond Seltzer, New City, both of N.Y.

[73] Assignee: Ciba-Geigy Corporation, Ardsley, N.Y.

[21] Appl. No.: 480,174

[22] Filed: Feb. 14, 1990

Related U.S. Application Data

[63] Continuation-in-part of Ser. No. 326,851, Mar. 21, 1989, abandoned.

[51] Int. Cl.$^5$ .................. C08K 5/3435; C07D 215/00; C07F 9/06
[52] U.S. Cl. ..................................... 524/99; 524/102; 524/103; 546/16; 546/22; 546/25
[58] Field of Search .................. 524/99, 102, 103; 546/16, 22, 25, 188

[56] References Cited

U.S. PATENT DOCUMENTS

| | | | |
|---|---|---|---|
| 4,096,114 | 6/1978 | Minagawa et al. | 524/99 |
| 4,661,594 | 4/1987 | Rasberger et al. | 524/99 |
| 4,665,185 | 5/1987 | Winter et al. | 546/184 |
| 4,808,645 | 2/1989 | Ravichandran et al. | 524/99 |

OTHER PUBLICATIONS

Shlyapintokh et al., "Developments in Polymer Stabilization", V, 41–70, (1982).

*Primary Examiner*—Kriellion Morgan
*Attorney, Agent, or Firm*—Luther A. R. Hall

[57] ABSTRACT

N-Hydrocarbyloxy derivatives of phosphorus substituted 4-amino- and 4-hydroxy-2,2,6,6-tetramethylpiperidine are effective light stabilizers for polymer compositions. These phosphorus compounds include phosphites and cyclic phosphites such as 1,3,2-dioxaphospholanes, 1,3,2-dioxaphosphorinanes, 1,3,2-oxazaphospholidines, 1,3,2-diazaphospholidines, 1,3,2-dioxaphosphocins, 1,3,2-dioxaphosphepins and 2,4,8,10-tertraoxa-3,9-diphosphaspiro[5,5]-undecanes.

39 Claims, No Drawings

_5,021,481_

N-HYDROCARBYLOXY HINDERED AMINE LIGHT STABILIZERS WITH PHOSPHORUS MOIETIES

This is a continuation-in-part application of Pat. application Ser. No. 326,851, filed on Mar. 21, 1989, now abandoned.

OBJECTS OF THE INVENTION

One object of the instant invention is to provide N-hydrocarbyloxy hindered amine light stabilizers substituted by trivalent phosphorus moieties.

Another object of the instant invention is to provide compositions of polymers subject to the deleterious effects of actinic light stabilized by an effective stabilizing amount of said N-hydrocarbyloxy hindered amine light stabilizer containing a phosphorus moiety.

DETAILED DISCLOSURE

The instant invention pertains to an N-hydrocarbyloxy hindered amine substituted by a trivalent phosphorus moiety having a formula I, II, III, IV or V

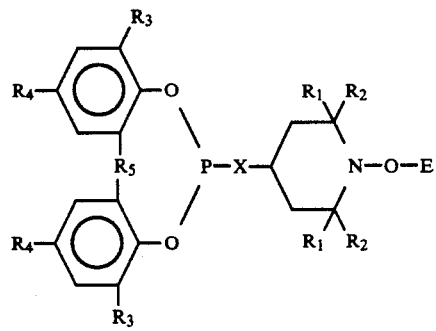  (I)

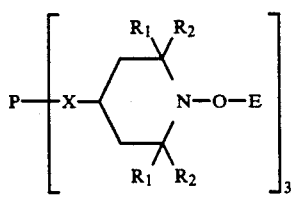  (II)

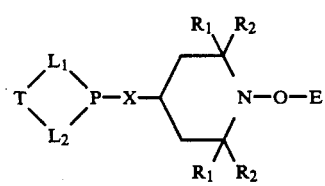  (III)

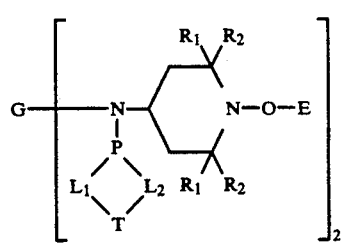  (IV)

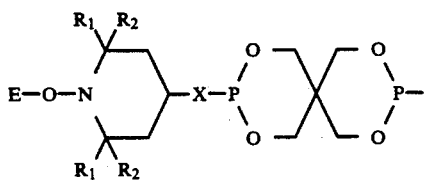  (V)

-continued

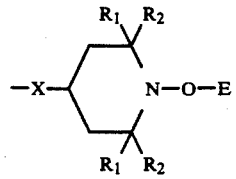

wherein $R_1$ and $R_2$ are independently methyl or ethyl or $R_1$ and $R_2$ together are pentamethylene, $R_3$ and $R_4$ are independently alkyl of 1 to 4 carbon atoms, $R_5$ is a direct bond, methylene or 1,1-alkylidene of 2 to 5 carbon atoms, X is hydrogen or alkyl of 1 to 18 carbon atoms, or X is

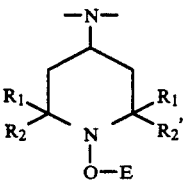

$L_1$ and $L_2$ are independently —O— or —NY— where Y is hydrogen or alkyl of 1 to 18 carbon atoms, or $L_1$ and $L_2$ are independently

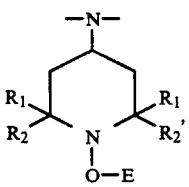

T is alkylene of 2 or 3 carbon atoms or said alkylene substituted by one or two alkyl groups each of 1 to 4 carbon atoms, G is alkylene of 2 to 12 carbon atoms, and E is alkyl of 1 to 18 carbon atoms, cycloalkyl of 5 to 12 carbon atoms, alkenyl of 2 to 18 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl.

Preferably $R_1$ and $R_2$ are each methyl.

Preferably $R_3$ and $R_4$ are independently methyl or tert-butyl, most preferably tert-butyl.

$R_5$ is preferably a direct bond or methylene, most preferably methylene.

X is preferably —O— or —NY— where Y is n-butyl or dodecyl, or X is

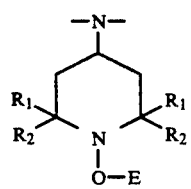

where $R_1$ and $R_2$ are each methyl.

Preferably $L_1$ and $L_2$ are independently —O— or —NY— where Y is tert-butyl, most preferably where $L_1$ and $L_2$ are each —O— or one of $L_1$ and $L_2$ is —O— and the other is —NY— where Y is tert-butyl.

T is preferably ethylene or 2,2-dimethyltrimethylene.

G is preferably hexamethylene.

Preferably E is alkyl of 1 to 9 carbon atoms, cyclohexyl or alpha-methylbenzyl, most preferably methyl, heptyl, octyl, cyclohexyl or alpha-methylbenzyl.

Synthesis

The preparation of 1-benzyloxy-4-hydroxy-2,2,6,6-tetramethylpiperidine and 1-cyclohexyloxy-2,2,6,6-piperidin-4-one is described by J.F.W. Keana et al, J. Org. Chem, 36, 209 (1971) and DW Grattan et al, Poly. Degrad Stability, 1979, 69.

N-Methoxypiperidine derivatives are synthesized by reaction of an appropriate N-oxyl precursor with methyl radicals generated by the thermolysis of di-tert-butyl peroxide in an inert solvent such as chlorobenzene.

N-Hydroxypiperidines, prepared by the oxidation of a hindered amine with a hydroperoxide and metal oxide catalyst (U.S. Pat. No. 4,665,185) followed by catalytic hydrogenation (copending Pat. application Ser. No. 099,418) now abandoned, are alkylated by reaction with sodium hydride and an alkyl iodide as taught by T. Kurumada et al, J. Poly Sci, Poly Chem. Ed, 23, 1477 (1985).

The preferred method of generation of N-hydrocarbyloxypiperidine derivatives of higher molecular weight hydrocarbons such as cyclohexane or ethylbenzene is the thermal reaction of a hydrocarbon solution of the hindered amine or its N-oxyl derivative with tert-butyl hydroperoxide and a metal oxide catalyst (copending Pat. application Ser. No. 259,949) now abandoned.

The 4-alkylamino derivatives of 1-hydrocarbyloxy piperidines are prepared by the reductive amination of the corresponding 4-oxopiperidine using sodium cyanoborohydride or catalytic hydrogenation.

U.S. Pat. No. 4,661,594 teaches the reaction of 4-amino- and 4-hydroxypiperidine derivatives with phosphochloridites in the presence of an inert solvent such as tetrahydrofuran or toluene and a base such as triethylamine. Azaphosphochloridites and diazaphosphochloridites containing N-piperidyl substituents are prepared by reductive amination of 4-oxopiperidine with the appropriate diamine or aminoalcohol followed by reaction with phosphorus trichloride.

The intermediates required to prepare the instant compounds are largely items of commerce.

Although the instant application emphasizes the 2,2,6,6-tetraalkylpiperidine structure, it is to be noted that the invention also relates to compounds wherein the following tetraalkyl substituted piperazine or piperazinone moieties are substituted for the above-noted tetraalkylpiperidine moiety:

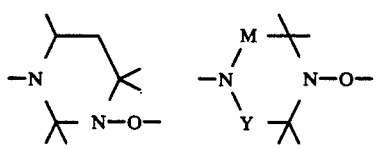

wherein M and Y are independently methylene or carbonyl, preferably M being methylene and Y being carbonyl It is understood that the identified substituents applicable to such compounds are those which are appropriate for substitution on the ring nitrogen atoms.

Substrates in which the compounds of this invention are particularly useful are polyolefins such as polyethylene and polypropylene; polystyrene, including especially impact polystyrene; ABS resin; elastomers such as e.g. butadiene rubber, EPM, EPDM, SBR and nitrile rubber.

In general polymers which can be stabilized include

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under 1), for example mixtures of polypropylene with polyisobutylene.

3. Copolymers of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene-norbornene.

4. Polystyrene, poly-(p-methylstyrene).

5. Copolymers of styrene or methylstyrene with dienes or acrylic derivatives, such as, for example, styrene/butadiene, styrene/acrylonitrile, styrene/ethyl methacrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block polymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as for example styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under 5) for instance the copolymer mixtures known as ABS-, MBS- ASA- or AES-polymers.

7. Halogen-containing polymers, such as polychloroprene, chlorinated rubbers, chlorinated or sulfochlorinated polyethylene, epichlorohydrin homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate, vinylidene chloride/vinyl acetate copolymers, or vinyl fluoride/vinyl ether copolymers.

8. Polymers which are derived from $\alpha,\beta$-unsaturated acids and derivatives thereof, such as polyacrylates and polymethacrylates, polyacrylamide and polyacrylonitrile.

9. Copolymers from the monomers mentioned under 8) with each other or with other unsaturated monomers, such as, for instance, acrylonitrile/butadiene, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as comonomer.

13. Polyphenylene oxides and sulfides, and mixtures of polyphenylene oxides with polystyrene.

14. Polyurethanes which are derived from polyethers, polyesters or polybutadienes with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4-trimethylhexamethylene terephthalamide, poly-p-phenylene terephthalamide or poly-m-phenylene isophthalamide, as well as copolymers thereof with polyethers, such as for instance with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2-(4-hydroxyphenyl)-propane] terephthalate and polyhydroxybenzoates as well as block-copolyether-esters derived from polyethers having hydroxyl end groups.

18. Polycarbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyl resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or silicone-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatin and derivatives thereof which are chemically modified in a polymer homologous manner, such as cellulose acetates, cellulose propionates and cellulose butyrates, or the cellulose ethers, such as methyl cellulose.

27. Mixtures of polymers as mentioned above, for example PP/EPDM, Polyamide 6/EPDM or ABS, PVC/EVA, PVC/ABS, PVC/MBS, PC/ABS, PBTP/ABS.

28. Naturally occurring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellitates) and also mixtures of synthetic esters with mineral oils in any weight ratios, which materials may be used as plasticizers for polymers or as textile spinning oils, as well as aqueous emulsions of such materials.

29. Aqueous emulsions of natural or synthetic rubber, e.g. natural latex or latices of carboxylated styrene/butadiene copolymers.

30. Polysiloxanes such as the soft, hydrophilic polysiloxanes described, for example, in U.S Pat. No. 4,259,467; and the hard polyorganosiloxanes described, for example, in U.S. Pat. No. 4,355,147.

31. Polyketimines in combination with unsaturated acrylic polyacetoacetate resins or with unsaturated acrylic resins. The unsaturated acrylic resins include the urethane acrylates, polyether acrylates, vinyl or acryl copolymers with pendant unsaturated groups and the acrylated melamines. The polyketimines are prepared from polyamines and ketones in the presence of an acid catalyst 32. Radiation curable compositions containing ethylenically unsaturated monomers or oligomers and a polyunsaturated aliphatic oligomer.

33. Epoxymelamine resins such as light-stable epoxy resins crosslinked by an epoxy functional coetherified high solids melamine resin such as LSE 4103 (Monsanto).

In general, the compounds of the present invention are employed in from about 0.01 to about 5% by weight of the stabilized composition, although this will vary with the particular substrate and application. An advantageous range is from about 0.5 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The resulting stabilized polymer compositions of the invention may optionally also contain various conventional additives, such as the following.

1. Antioxidants

1.1. Alkylated monophenols, for example, 2,6-di-tert-butyl-4-methylphenol
2-tert-butyl-4,6-dimethylphenol
2,6-di-tert-butyl-4-ethylphenol
2,6-di-tert-butyl-4-n-butylphenol
2,6-di-tert-butyl-4-i-butylphenol
2,6-di-cyclopentyl-4-methylphenol
2-(α-methylcyclohexyl)-4,6-dimethylphenol
2,6-di-octadecyl-4-methylphenol
2,4,6-tri-cyclohexylphenol
2,6-di-tert-butyl-4-methoxymethylphenol

1.2. Alkylated hydroquinones, for example, 2,6-di-tert-butyl-4-methoxyphenol
2,5-di-tert-butyl-hydroquinone
2,5-di-tert-amyl-hydroquinone
2,6-diphenyl-4-octadecyloxyphenol

1.3. Hydroxylated thiodiphenyl ethers, for example 2,2'-thio-bis-(6-tert-butyl-4-methylphenol)
2,2'-thio-bis-(4-octylphenol)
4,4'-thio-bis-(6-tert-butyl-3-methylphenol)
4,4'-thio-bis-(6-tert-butyl-2-methylphenol)

1.4. Alkylidene-bisphenols, for example, 2,2'-methylene-bis-(6-tert-butyl-4-methylphenol)
2,2'-methylene-bis-(6-tert-butyl-4-ethylphenol)
2,2'-methylene-bis-[4-methyl-6-(α-methylcyclohexyl)-phenol]
2,2'-methylene-bis-(4-methyl-6-cyclohexylphenol)
2,2'-methylene-bis-(6-nonyl-4-methylphenol)
2,2'-methylene-bis-[6-(α-methylbenzyl)-4-nonylphenol]
2,2'-methylene-bis-[6-(α,α-dimethylbenzyl)-4-nonylphenol]
2,2'-methylene-bis-(4,6-di-tert-butylphenol)
2,2'-ethylidene-bis-(4,6-di-tert-butylphenol)
2,2'-ethylidene-bis-(6-tert-butyl-4-isobutylphenol)
4,4'-methylene-bis-(2,6-di-tert-butylphenol)
4,4'-methylene-bis-(6-tert-butyl-2-methylphenol)
1,1-bis-(5-tert-butyl-4-hydroxy-2-methylphenyl-butane
2,6-di-(3-tert-butyl-5-methyl-2-hydroxybenzyl)-4-methylphenol
1,1,3-tris-(5-tert-butyl-4-hydroxy-2-methylphenyl)-butane
1,1-bis-(5-tert-butyl-4-hydroxy-2-methylphenyl)-3-n-dodecylmercaptobutane
ethyleneglycol bis-[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methyl-benzyl)-6-tert-butyl-4-methylphenyl] terephthalate.

1.5. Benzyl compounds, for example, 1,3,5-tri-(3,5-di-tert-butyl-4-hydroxybenzyl)-2,4,6-trimethylbenzene
di-(3,5-di-tert-butyl-4-hydroxybenzyl) sulfide
3,5-di-tert-butyl-4-hydroxybenzyl-mercapto-acetic acid isooctyl ester
bis-(4-tert-butyl-3-hydroxy-2,6-dimethylbenzyl)dithiol terephthalate
1.3,5-tris-(3,5-dl-tert-butyl-4-hydroxybenzyl) isocyanurate
1,3,5-tris-(4-tert-butyl-3-hydroxy-2,6-dimethylbenzyl) isocyanurate
3,5-di-tert-butyl-4-hydroxybenzyl-phosphoric acid dioctadecyl ester
3,5-di-tert-butyl-4-hydroxybenzyl-phosphoric acid monoethyl ester, calcium-salt

1.6. Acylaminophenols, for example, 4-hydroxy-lauric acid anilide
4-hydroxy-stearic acid anilide
2,4-bis-octylmercapto-6-(3,5-tert-butyl-4-hydroxyanilino)-s-triazine
octyl-N-(3,5-di-tert-butyl-4-hydroxyphenyl)-carbamate

1.7. Esters of β-(3,5-di-tert-butyl-4-hydroxyphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.8. Esters of β-(5-tert-butyl-4-hydroxy-3-methylphenyl)-propionic acid with monohydric or polyhydric alcohols, for example,

| | |
|---|---|
| methanol | diethylene glycol |
| octadecanol | triethylene glycol |
| 1,6-hexanediol | pentaerythritol |
| neopentyl glycol | tris-hydroxyethyl isocyanurate |
| thiodiethylene glycol | di-hydroxyethyl oxalic acid diamide |

1.9. Amides of β-(3,5-di-tert-butyl-4-hydroxyphenyl)-propionic acid for example, N,N'-di-(3,5-di-tert-butyl-4-hydroxyphenylpropionyl)-hexamethylenediamine
N,N'-di-(3,5-di-tert-butyl-4-hydroxyphenylpropionyl)-trimethylenediamine
N,N'-di-(3,5-di-tert-butyl-4-hydroxyphenylpropionyl)-hydrazine

2. UV absorbers and light stabilizers

2.1. 2-(2'-Hydroxyphenyl)-benzotriazoles, for example, the

5'-methyl-, 3',5'-di-tert-butyl-, 5'-tert-butyl-,
5'-(1,1,3,3-tetramethylbutyl)-, 5-chloro-3',5'-di-tert-butyl-,
5-chloro-3'-tert-butyl-5'-methyl-, 3'-sec-butyl-5'-tert-butyl-,
4'-octoxy, 3',5'-di-tert-amyl-, 3',5'-bis-(α,α-dimethylbenzyl),
3'-tert-butyl-5'-(2-(omega-hydroxy-octa-(ethyleneoxy)carbonyl-ethyl)-,
3'-dodecyl-5'-methyl-,
and 3'-tert-butyl-5'-(2-octyloxycarbonyl)ethyl-, and dodecylated-5'-methyl derivatives.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy- and 2'-hydroxy-4,4'-dimethoxy derivatives.

2.3. Esters of optionally substituted benzoic acids for example, phenyl salicylate, 4-tert-butylphenyl salicylate, octylphenyl salicylate, dibenzoylresorcinol, bis-(4-tert-butylbenzoyl)-resorcinol, benzoylresorcinol, 3,5-di-tert-butyl-4-hydroxybenzoic acid 2,4-di-tert-butylphenyl ester and 3,5-di-tert-butyl-4-hydroxybenzoic acid hexadecyl ester.

2.4. Acrylates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyano-vinyl)-2-methyl-indoline.

2.5 Nickel compounds, for example, nickel complexes of 2,2'-thio-bis-[4-(1,1,3,3-tetramethylbutyl)-phenol], such as the 1:1 or 1:2 complex, optionally with additional ligands such as n-butylamine, triethanolamine or N-cyclohexyl-diethanolamine, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy-4-methyl-phenyl undecyl ketoxime, nickel complexes of 1-phenyl-4-lauroyl-5-hydroxy-pyrazole, optionally with additional ligands.

2.6. Sterically hindered amines, for example bis-(2,2,6,6-tetramethylpiperidyl) sebacate, bis-(1,2,2,6,6-pentamethylpiperidyl) sebacate, n-butyl-3,5-di-tert.butyl-4-hydroxybenzyl malonic acid bis-(1,2,2,6,6-pentamethylpiperidyl)ester, condensation product of 1-hydroxyethyl-2,2,6,6-tetramethyl-4-hydroxypiperidine and succinic acid, condensation product of N,N'-(2,2,6,6-tetramethylpiperidyl)-hexamethylenediamine and 4-tert-octylamino-2,6-dichloro-s-triazine, tris(2,2,6,6-tetramethylpiperidyl)-nitrilotriacetate, tetrakis-(2,2,6,6-tetramethyl-4-piperidyl)-1,2,3,4-butanetetracarbonic acid, 1,1'(1,2-ethanediyl)-bis-(3,3,5,5tetramethylpiperazinone).

2.7. Oxalic acid diamides, for example, 4,4'-dioctyloxyoxanilide, 2,2'-di-octyloxy-5,5'-di-tert-butyloxanilide, 2,2'-di-dodecyloxy-5,5'-di-tert-butyl-oxanilide, 2-ethoxy-2'-ethyl-oxanilide, N,N'-bis (3-dimethylaminopropyl)-oxalamide, 2-ethoxy-5-tert-butyl-2'-ethyloxanilide and its mixture with 2-ethoxy-2'-ethyl-5,4'-di-tert-butyloxanilide and mixtures of ortho- and para-methoxy-as well as of o-and p-ethoxy-disubstituted oxanilides.

2.8. Hydroxyphenyl-s-triazines, for example 2,6-bis-(2,4-dimethylphenyl) -4-(2-hydroxy-4-octyloxyphenyl)-s-triazine; 2,6-bis-(2,4-dimethylphenyl)-4-(2,4-dihydroxyphenyl)-striazine; 2,4-bis(2,4-dihydroxyphenyl)-6-(4-chlorophenyl)-s-triazine; 2,4-bis[2-hydroxy-4-(2-hydroxyethoxy)phenyl]-6-(4-chlorophenyl)-s-triazine; 2,4-bis[2-hydroxy-4-(2-hydroxyethoxy)phenyl] -6-phenyl-s-triazine; 2,4-bis[2-hydroxy-4-(2-hydroxyethoxy-phenyl]-6-(2,4-dimethylphenyl)-s-triazine; 2,4-bis[2-hydroxy-4-(2-hydroxyethoxy)phenyl]-6-(4-bromophenyl)-s-triazine; 2,4-bis[2-hydroxy-4-(2-acetoxyethoxy)phenyl] -6-(4-chlorophenyl)-s-triazine, 2,4-bis(2,4-dihydroxyphenyl)-6-(2,4-dimethylphenyl)-s-triazine.

3. Metal deactivators, for example, N,N'-diphenyloxalic acid diamide, N-salicylal-N'-salicyloylhydrazine, N,N'-bis-salicyloylhydrazine, N,N'-bis-(3,5-di-tert-butyl4-hydroxyphenylpropionyl)-hydrazine, 3-salicyloylamino-1,2,4-triazole, bis-benzylidene-oxalic acid dihydrazide.

4. Phosphites and phosphonites, for example, triphenyl phosphite, diphenylalkyl phosphites, phenyldialkyl phosphites, tri-(nonylphenyl) phosphite, trilauryl phosphite, trioctadecyl phosphite, di-stearyl-pentaerythritol diphosphite, tris-(2,4-di-tert-butylphenyl) phosphite, di-isodecylpentaerythritol diphosphite, di-(2,4-di-tertbutylphenyl)pentaerythritol diphosphite, tristearyl sorbitol triphosphite, tetrakis-(2,4-di-tert-butylphenyl) 4,4'-diphenylylenediphosphonite.

5. Compounds which destroy peroxide, for example esters of β-thiodipropionic acid, for example the lauryl, stearyl, myristyl or tridecyl esters, mercapto-benzimidazole or the zinc salt of 2-mercaptobenzimidazole, zinc dibutyl-dithiocarbamate, dioctadecyl disulfide, pentaerythritol tetrakis-(β-dodecylmercapto)-propionate.

6. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

7. Polyamide stabilizers, for example copper salts in combination with iodides and/or phosphorus compounds and salts of divalent manganese.

8. Basic co-stabilizer, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example Ca stearate, Zn stearate, Mg stearate, Na ricinoleate and K palmitate, antimony pyrocatecholate or zinc pyrocatecholate.

9. Nucleating agents, for example, 4-tert-butyl-benzoic acid, adipic acid, diphenylacetic acid.

10. Fillers and reinforcing agents, for example, calcium carbonate, silicates, glass fibers, asbestos, talc, kaolin, mica, barium sulfate, metal oxides and hydroxides, carbon black, graphite 11. Other Additives, for example, plasticizers, lubricants, emulsifiers, pigments, optical brighteners, flameproofing agents, anti-static agents, blowing agents and thiosynergists such as dilauryl thiodipropionate or distearyl thiodipropionate.

Of particular interest is the utilization of the instant derivatives in a variety of coating systems including ambient cured and acid catalyzed coating systems. In particular, the physical integrity of the coatings is maintained to a higher degree with significant reduction in loss of gloss and yellowing. Key improvements include the substantial absence of the cure retardation encountered with N-alkyl hindered amine light stabilizers; the substantial absence of flocculation and dispersion destabilization seen when N-alkyl hindered amines are utilized in certain piqmented coating systems and the absence of adhesion loss between the coating and polycarbonate substrate. Accordingly, the present invention also relates to the use of the instant compounds, optionally together with further stabilizers, for stabilizing ambient cured coatings based on alkyd resins; thermoplastic acrylic resins; acrylic alkyls; acrylic alkyd or polyester resins optionally modified with silicon, isocyanates, isocyanurates, ketimines or oxazolidines; and epoxide resins crosslinked with carboxylic acids, anhydrides, polyamines or mercaptans; and acrylic and polyester resin systems modified with reactive groups in the backbone thereof and crosslinked with epoxides; against the degradative effects of light, moisture and oxygen Furthermore, in their industrial uses, enamels with high solids content based on crosslinkable acrylic, polyester, urethane or alkyd resins are cured with an additional acid catalyst Light stabilizers containing a basic nitrogen group are generally less than satisfactory in this application. Formation of a salt between the acid catalyst and the light stabilizer leads to incompatibility or insolubility and precipitation of the salt and to a reduced level of cure and to reduced light protective action and poor resistance to moisture.

These acid catalyzed stoving lacquers are based on hot crosslinkable acrylic, polyester, polyurethane, polyamide or alkyd resins The acrylic resin lacquers, which can be stabilized against light, moisture and oxygen in accordance with the invention, are the conventional acrylic resin stoving lacquers or thermosetting resins including acrylic/melamine systems which are described, for example, in H. Kittel's "Lehrbuch der Lacke und Beschichtungen", Vol 1 Par 2, on pages 735 and 742 (Berlin 1972), "Lackkunstharze" (1977), by H Wagner and H.F. Sarx, on pages 229–238, and in S Paul's "Surface Coatings: Science and Technology" (1985).

The polyester lacquers, which can be stabilized against the action of light and moisture, are the conventional stoving lacquers described e.g. in H. Wagner and H.F. Sarx, op. cit., on pages 86–99.

The alkyd resin lacquers which can be stabilized against the action of light and moisture in accordance with the invention, are the conventional stoving lacquers which are used in particular for coating automobiles (automobile finishing lacquers), for example lacquers based on alkyd/melamine resins and alkyd/acrylic/melamine resi (see H. Wagner and H F. Sarx, op. cit., pages 99–123). Other crosslinking agents include glycoluril resins, blocked isocyanates or epoxy resins.

The acid catalyzed stoving lacquers stabilized in accordance with the invention are suitable both for metal finish coatings and solid shade finishes, especially in the case of retouching finishes, as well s various coil coating applications The lacquers stabilized in accordance with the invention are preferably applied in the conventional manner by two methods, either by the single-coat method or by the two-coat method In the latter method, the pigment-containing base coat is applied first and then a covering coat of clear lacquer over it.

It is also to be noted that the instant substituted hindered amines are applicable for use in non-acid catalyzed thermoset resins such as epoxy, epoxy-polyester, vinyl, alkyd, acrylic and polyester resins, optionally modified with silicon, isocyanates or isocyanurates. The epoxy and epoxy-polyester resins are crosslinked with conventional crosslinkers such as acids, acid anhydrides, amines, and the like.

Correspondingly, the epoxide may be utilized as the crosslinking agent for various acrylic or polyester resin systems that have been modified by the presence of reactive groups on the backbone structure.

To attain maximum light stability in such coatings, the concurrent use of other conventional light stabilizers can be advantageous. Examples are the aforementioned UV absorbers of the benzophenone, benzotriazole, acrylic acid derivative, or oxanilide type, or aryl-s-triazines or metal-containing light stabilizers, for example organic nickel compounds. In two-coat systems, these additional light stabilizers can be added to the clear coat and/or the pigmented base coat.

If such combinations are employed, the sum of all light stabilizers is 0.2 to 20% by weight, preferably 0.5 to 5% by weight, based on the film-forming resin.

Examples of different classes of UV absorbers which may be used in the instant compositions in conjunction with the aforementioned piperidine compounds are referenced in a paper by H. J. Heller in European Polymer Journal Supplement, 1969, pp. 105–132. These classes include the phenyl salicylates, the o-hydroxybenzophenones, the hydroxyxanthones, the benzoxazoles, the benzimidazoles, the oxadiazoles, the triazoles, the pyrimidines, the chinazolines, the s-triazines, the hydroxyphenyl-benzotriazoles, the alpha-cyanoacrylates and the benzoates.

Types of UV absorbers of especial importance are:

(a) 2-(2′-Hydroxyphenyl)-benzotriazoles, for example, the 5′-methyl-, 3′,5′-di-tert-butyl-, 5′-tert-butyl-, 5′-(1,1,3,3-tetramethylbutyl)-, 5-chloro-3′,5′-di-tert-butyl-, 5-chloro-3′-tert-butyl-5′-methyl-, 3′-sec-butyl-5′-tert-butyl-, 4′-octoxy-, and 3′,5′-di-tert-amyl derivatives.

(b) 2-Hydroxy-benzophenones, for example, the 4-hydroxy-, 4-methoxy-, 4-octoxy-, 4-decyloxy-, 4-dodecyloxy-, 4-benzyloxy, 4,2′,4′-trihydroxy- and 2′-hydroxy-4,4′-dimethoxy derivatives.

(c) Acrylates, for example, alpha-cyano-β,β-diphenylacrylic acid ethyl ester or isoctyl ester alpha-carbo-methoxy-cinnamic acid methyl ester, alpha-cyano-β-methyl-p-methoxy-cinnamic acid methyl ester or butyl ester alpha-carbomethoxy-p-methoxy-cinnamic acid methyl ester, N-(β-carbomethoxy-β-cyanovinyl)-2-methyl-indoline.

(d) Nickel compounds, for example, nickel complexes of 2,2′-thiobis-[4-(1,1,3,3-tetramethylbutyl)-phenol], such as the 1:1 or 1:2 complex, optionally with additional ligands such as n-butylamine, triethanolamine or N-cyclo-hexyl-diethanolamie, nickel dibutyldithiocarbamate, nickel salts of 4-hydroxy-3,5-di-tert-butylbenzylphosphonic acid monoalkyl esters, such as of the methyl, ethyl or butyl ester, nickel complexes of ketoximes such as of 2-hydroxy4-methyl-phenyl undecyl ketonoxime, nickel complexes of 1-phenyl-4-lauroyl-5-hydroxy-pyrazol, optionally with additional ligands.

(e) Oxalic acid diamides, for example, 4,4′-di-octyloxyoxanilide, 2,2′-di-octyloxy-5,5′-di-tert-butyl-oxanilide, 2,2′-di-dodecyloxy-5,5′-di-tert-butyl-oxanilide, 2-ethoxy-2′-ethyl-oxanilide, N,N′-bis-(3-dimethylaminopropyl)-oxalamide, 2-ethoxy-5-tert-butyl-2′-ethyl-oxanilide and its mixture with 2-ethoxy-2′-ethyl-5,4′-di-tert-butyloxanilide and its mixtures of ortho- and para-methoxy- as well as of o- and p-ethoxy-disubstituted oxanilides.

(f) Hydroxyphenyl-s-triazines such as 2,6-bis(2,4-dimethylphenyl) -4-(2-hydroxy-4-octyloxyphenyl)-s-triazine or the corresponding 4-(2,4-dihydroxyphenyl) derivative.

Of particular value in the instant compositions are the benzotriazoles of high molecular weight and low volatility such as 2-[2-hydroxy-3,5-di(alpha,alpha-dimethylbenzyl)-phenyl]-2H-benzotriazole, 2-(2-hydroxy-3,5-di-tert-octylphenyl)-2H-benzotriazole, 2-(2-hydroxy-3-alpha, alpha-dimethylbenzyl-5-tert-octyl-phenyl)-2H-benzotriazole, 2-(2-hydroxy-3-tert-octyl-5-alpha,alpha-dimethylbenzylphenyl)-2H-benzotriazole, 2-(2-hydroxy-3,5-di-tert-amylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole, dodecylated 2-(2-hydroxy-5-methylphenyl)2H-benzotriazole, 2-[2-hydroxy-3-tert-butyl-5-(2-octyloxy-carbonyl)ethylphenyl]-2H-benzotriazole and the 5-chloro compounds corresponding to each of the above named benzotriazoles.

Most preferably the benzotriazoles useful in the instant compositions are 2-[2-hydroxy-3,5-di(alpha,alpha-dimethyl-benzyl)phenyl]-2H-benzotriazole, dodecylated 2-(2-hydroxy-5-methylphenyl)-2H-benzotriazole, 2-[2-hydroxy-3-tert-butyl-5-(2-(omega-hydroxy-octa-(ethyleneoxy) carbonyl)-ethylphenyl]-2H-benzotriazole 2-[2-hydroxy-3-tert-butyl-5-(2-octyl-oxycarbonyl) ethylphenyl]-2H-benzotriazole and 5-chloro-2-[2-hydroxy-3-tert-butyl-5-(2-octyloxycarbonyl)ethylphenyl] -2H-benzotriazole.

It is also contemplated that the instant compounds will be particularly effective as stabilizers for polyolefin fibers, especially polypropylene fibers, when used in conjunction with other stabilizers selected from the group consisting of the phenolic antioxidants, hindered amine light stabilizers, organic phosphorus compounds, ultraviolet absorbers and mixtures thereof.

A preferred embodiment of the instant invention pertains to stabilized compositions comprising
  (a) an acid catalyzed thermoset coating or enamel based on hot crosslinkable acrylic, polyester or alkyd resins,
  (b) a NOE-substituted 2,2,6,6-tetraalkylpiperidine compound, and
  (c) a UV absorber selected from the group consisting of the benzophenones, benzotriazoles, acrylic acid derivatives, organic nickel compounds, aryl-s-triazines and oxanilides.

Further ingredients which the enamels or coatings can contain are antioxidants, for example those of the sterically hindered phenol derivatives, phosphorus compounds, such as phosphites, phosphines or phosphonites, plasticizers, levelling assistants, hardening catalysts, thickeners, dispersants or adhesion promoters.

A further preferred embodiment of the instant invention is a stabilized composition containing components (a), (b) and (c) described above which additionally contains as component (d) a phosphite or phosphonite.

The amount of phosphite or phosphonite (d) which is used in the instant compositions is from 0.05 to 2% by weight, preferably from 0.1 to 1% by weight, based on the film forming resin. In two-coat systems, these stabilizers may be added to the clear coat and/or base coat.

Typical phosphite and phosphonites include triphenyl phosphite, diphenylalkyl phosphites, phenyldialkyl phosphites, tri-(nonylphenyl)phosphite, trilauryl phosphite trioctadecyl phosphite, di-stearyl-pentaerythritol diphosphite, tris-(2,4-di-tert.butylphenyl) phosphite, di-isodecylpentaerythritol diphosphite, di-(2,4-di-tert.butylphenyl)pentaerythritol diphosphite, tristearyl-sorbitol triphosphite, tetrakis-(2,4-di-tert.butylphenyl)-4,4'-diphenylenediphosphonite.

The acid catalyzed thermoset enamels must be stabilized in order to function acceptably in end-use applications. The stabilizers used are hindered amines, preferably those substituted on the N-atom by an inert blocking group in order to prevent precipitation of the basic amine stabilized with the acid catalyst with a concomitant retardation in cure, optionally in combination with UV absorbers, such as the benzotriazoles, benzophenones, substituted s-triazines, phenyl benzoates or oxanilides.

The stabilizers are needed to impart greater retention of durability to the cured enamels (as measured by 20° gloss, distinction of image, cracking or chalking); the stabilizers must not retard cure (normal bake for auto finishes at 121° C. and low bake repair at 82° C. (as measured by hardness, adhesion, solvent resistance and humidity resistance), the enamel should not yellow on curing and further color change on exposure to light should be minimized; the stabilizers should be soluble in the organic solvents normally used in coating applications such as methyl amyl ketone, xylene, n-hexyl acetate, alcohol and the like.

The instant hindered amine light stabilizers substituted on the N-atom by an O -substituted moiety fulfill each of these requirements and provide alone or in combination with a UV-absorber outstanding light stabilization protection to the cured acid catalyzed thermoset enamels.

Still another preferred combination of the instant stabilizers is with a hydroxylamine in order to protect polypropylene fibers from gas fading.

The following examples are presented for the purpose of illustration only and are not to be construed to limit the nature or scope of the instant invention in any manner whatsoever.

EXAMPLE 1A

4-Benzoyloxy-1-cyclohexyloxy-2,2,6,6-tetramethyl-piperidine

A mixture of 10.5 grams (40.2 mmol) of 4-benzoyloxy2,2,6,6 tetramethylpiperidine, 16.1 grams (160.8 mmol) of 90% tert-butyl hydroperoxide, 600 mg of molybdenum trioxide and 60 ml of cyclohexane is placed in a Fischer-Porter pressure bottle (under a nitrogen atmosphere in an oil bath. The bath temperature is gradually increased to 135° C. over a 2.25 hour period and then maintained at 135° C. for another 2.25 hours till the red color of the N-oxyl intermediate is discharged. Solids are removed by filtration. The cyclohexane solution is washed twice with water, washed with saturated sodium chloride solution, dried over anhydrous magnesium sulfate and concentrated under reduced pressure to yield an oil. Purification of the oil by flash chromatography (silica gel; 100:3 heptane:ethyl acetate) affords 12.8 grams of the title compound.

Analysis:
Calcd for $C_{22}H_{33}NO_3$: C, 73.5; H, 9.2; N, 3.9.
Found: C, 73.2; H, 9.2; N, 3.8.

EXAMPLE 1B

1-Cyclohexyloxy-4-hydroxy-2,2,6,6-tetramethylpiperidine

The ester obtained in Example 1A is hydrolyzed using potassium hydroxide and aqueous methanol to give the title compound as a white solid melting at 74–78° C.

Analysis:
Calcd for $C_{15}H_{29}NO_2$: C, 70.5; H, 11.5; N, 5.5.
Found: C, 70.3; H, 11.3; N, 5.4.

EXAMPLE 1C 2,4,8,10-Tetra-tert-butyl-6-(1-cyclohexyloxy-2,2,6,6-tetramethyl-piperidin-4-yloxy)-12H-dibenzo [d,g][1,3,2]dioxaphosphocin A solution of 7.8 grams (30.5 mmol) of 1-cyclohexyloxy-4-hydroxy-2,2,6,6-tetramethylpiperidine, 3.1 grams (30.6 mmol) of triethylamine and 75 ml of tetrahydrofuran is added over 30 minutes to chilled (5° C.) suspension of 15.0 grams (30.7 mmol) of 2,4,8,10-tetra-tert-butyl6-chloro-12H-dibenzo [d,g][1,3,2]dioxaphosphocin in 100 ml of tetrahydrofuran. The reaction temperature increases to 13° C. during the addition of the alcohol. The reaction mixture is stirred overnight at room temperature. Triethylamine hydrochloride is removed by filtration, and the filtrate is concentrated at reduced pressure to obtain a glass. Crystallization from acetonitrile affords 18.3 grams (85% yield) of the title compound as a white solid melting at 140–144° C. 31p nmr (benzene-d$_6$): δ130.2 (85% phosphoric acid external standard)

Analysis:
Calcd for C$_{44}$H$_{70}$NO$_4$P: C, 74.6; H, 10.0; N, 2.0.
Found: C, 74.4; H, 9.9; N, 2.0.

EXAMPLE 2A

4-Hydroxy-1-alpha-methylbenzyloxy-2,2,6,6-tetramethylpiperidine

70% Aqueous tert-butyl hydroperoxide (74.8 grams, 609 mmol) is added over 30 minutes to a mixture of 35.0 grams (203 mmol) of 4-hydroxy-1-oxyl-2,2,6,6-tetramethylpiperidine, 2.0 grams of molybdenum trioxide and 200 ml of ethylbenzene which is heated to 120° C. The reaction mixture is maintained at reflux throughout the addition and water is collected in a Dean-Stark trap. The red mixture is heated at reflux for three hours after the addition is complete in order to discharge the red color of the N-oxyl compound. Solids are removed by filtration and the filtrate is concentrated at reduced pressure to obtain a yellow oil. Purification of the oil by flash chromatography (silica gel; 4:1 hexane:ethylacetate) affords 30.0 grams (53% yield) of the title compound as a white solid melting at 95–97° C.

Analysis:
Calcd for C$_{17}$H$_{27}$NO$_2$: C, 73.6; H, 9.8; N, 5.0.
Found: C, 73.4; H, 9.8; N, 5.0.

EXAMPLE 2B 2,4,8,10-Tetra-tert-butyl-6-(1-alpha-methylbenzyloxy2,2,6,6-tetramethylpiperidin-4-yloxy)-12H-dibenzo[d,g][1,3,2]dioxaphosphocin The title compound which is a white solid melting at 168–172° C. is prepared in 80% yield from 4-hydroxy-1-alpha-methylbenzyloxy -2,2,6,6-tetramethylpiperidin according to the procedure of Example 1C.

31$_p$ nmr (benzene-d$_6$): δ130.7
Calcd for C$_{46}$H$_{68}$NO$_4$P: C, 75.7; H, 9.4; N, 1.9.
Found: C, 75.5; H, 9.5; N, 2.0.

EXAMPLE 3A

4-Benzoyloxy-1-ethoxy-2,2,6,6-tetramethylpiperidine

A mixture of 28.3 grams (102 mmol) of 4-benzoyloxy-1-oxyl-2,2,6,6-tetramethylpiperidine, 5.0 grams of magnesium sulfate, 1.0 gram of 5% palladium on carbon, and 100 ml of anhydrous tetrahydrofuran is hydrogenated (50 psi, room temperature) in a Parr apparatus. Solids are removed by filtration, and ethyl iodide (32.1 grams, 206 mmol) is added to the crude hydroxylamine solution. A solution obtained by refluxing a suspension of 3.7 grams (154 mmol) of sodium hydride in 50 ml of dimethyl sulfoxide and 50 ml of tetrahydrofuran is then added over 30 minutes to the hydroxylamine solution. The reaction mixture is diluted with water (1000 ml) and extracted with ether (2×150 ml). The combined organic layers are washed with water (2×1000 ml), washed with saturated sodium chloride solution (500 ml), dried over anhydrous magnesium sulfate, and concentrated under reduced pressure. The crude product is purified by flash chromatography (silica gel; 9:1 hexane:ethyl acetate) and crystallized from methanol to afford 15.1 grams (48% yield) of the title compound as a white solid melting at 76–78° C.

Analysis:
Calcd for C$_{18}$H$_{27}$NO$_3$:C, 70.8; H, 8.9; N, 4.6.
Found: C, 71.2; H, 9.1; N, 4.5.

EXAMPLE 3B

1-Ethoxy-4-hydroxy-2,2,6,6-tetramethylpiperidine

The ester obtained in Example 3A is hydrolyzed using sodium hydroxide and aqueous methanol to give the title compound as a white solid melting at 86–88° C.

Analysis:
Calcd for C$_{11}$H$_{23}$NO$_2$:C, 65.6; H, 11.5; N, 7.0.
Found: C, 66.0; H, 11.8; N, 7.0.

EXAMPLE 3C 2,4,8,10-Tetra-tert-butyl-6-(1-ethoxy-2,2,6,6-tetramethyl-piperidin-4-yloxy)-12H-dibenzo[d,g][1,3,2]dioxaphosphocin The title compound is a white solid melting at 187–189° C. prepared in 57% yield from 1-ethoxy-4-hydroxy2,2,6,6-tetramethylpiperidine according to the procedure of Example 1C.

31$_p$ nmr (benzene-d$_6$): δ130.7
Analysis:
Calcd for C$_{40}$H$_{64}$NO$_4$P: C, 73.5; H, 9.9; N, 2.1.
Found: C, 73.5; H, 10.1; N, 2.1.

EXAMPLE 4

2,4,8,10-Tetra-tert-butyl-6-(1-benzyloxy-2,2,6,6-tetramethylpiperidin-4-yloxy)-12H-dibenzo[d,g][1,3,2]dioxaphosphocin The title compound is a white solid melting at 175–178° C. prepared in 84% yield from 1-benzyloxy4-hydroxy-2,2,6,6-tetramethylpiperidine according to the procedure of Example 1C.

31$_p$ nmr (benzene-d$_6$): δ130.7
Analysis:
Calcd for C$_{45}$H$_{66}$NO$_4$P: C, 75.5; H, 9.3; N, 2.0.
Found: C, 75.5; H, 9.5; N, 2.0.

EXAMPLE 5A

4-Benzoyloxy-1-methoxy-2,2,6,6-tetramethylpiperidine

A solution of 20.0 grams (72 mmol) of 4-benzoyloxy-1-oxyl-2,2,6,6-tetramethylpiperidine, 10.5 grams (72 mmol) of di-tert-butyl peroxide, and 30 ml of chlorobenzene is heated for six hours in a Fischer-Porter pressure bottle (nitrogen atmosphere, bath temperature 145–150° C.). The crude reaction product is purified by flash chromatography (silica gel; 50:1 heptane:ethyl acetate) and then recrystallized from methanol to afford 10.8 grams (51% yield) of the title compound as a white solid melting at 67–68° C.

Analysis:
Calcd for C$_{12}$H$_{25}$NO$_3$: C, 70.1; H, 8.7; N, 4.8.
Found: C, 70.0; H, 8.8; N, 4.8.

EXAMPLE 5B

4-Hydroxy-1-methoxy-2,2,6,6-tetramethylpiperidine

The ester obtain in Example 5A is hydrolyzed using potassium hydroxide and aqueous methanol to give the title compound as a white solid melting at 92–93° C.

Example 5C

2,4,8,10-Tetra-tert-butyl-6-(1-methoxy-2,2,6,6-tetramethyl-piperidin-4-yloxy)-12H-dibenzo[d,g][1,3,2]dioxaphosphocin The title compound is a white solid melting at 203–205° C. prepared in 88% yield from 4-hydroxy-1-methoxy-2,2,6,6-tetramethylpiperidine according to the procedure of Example 1C.

$31_p$ nmr (benzene-$d_6$): $\delta$130.2
Analysis:
Calcd for $C_{39}H_{62}NO_4P$: C, 73.2; H, 9.8; N, 2.2.
Found: C, 73.3; H, 9.6; N, 2.2.

EXAMPLE 6

3-tert-Butyl-2-(1-alpha-methylbenzyloxy-2,2,6,6-tetramethyl-piperidin-4-yloxy)-1,3,2-oxazaphospholidine A solution of 9.8 grams (54 mmol) of 3-tert-butyl-2-chloro-1,3,2-oxazaphospholidine in 40 ml of tetrahydrofuran is added dropwise over 30 minutes to a solution of 15.0 grams (54 mmol) of 4-hydroxy-1-alpha-methylbenzyloxy-2,2,6,6-tetramethylpiperidine, prepared in Example 2A, 6.0 grams (159 mmol) of triethylamine and 80 ml of tetrahydrofuran. The reaction temperature increases from 20° C. to 32° C. during the addition. The reaction mixture is stirred for three hours after the addition is complete. Triethylamine hydrochloride is removed by filtration, and the filtrate is concentrated under reduced pressure to yield an oil. Trituration of the crude product with hexane affords 9.3 grams (41% yield) of the title compound as a white solid melting at 110–113° C.

$31_p$ nmr (benzene-$d_6$): $\delta$133.7
Analysis:
Calcd for $C_{23}H_{39}NO_3P$: C, 65.4; H, 9.3; N, 6.6.
Found: C, 65.0; H, 9.1; N, 6.6.

EXAMPLE 7

3-tert-Butyl-2-(1-methoxy-2,2,6,6-tetramethylpiperidin-4-yloxy)-1,3,2-oxazaphospholidine The title compound is prepared from 4-hydroxy-1-methoxy-2,2,6,6-tetramethylpiperidine (prepared in Example 5B) according to the procedure of Example 6. Purification of the crude product by distillation affords an 80% yield of a white solid melting at 54–56° C. and having a boiling point of 130–140° C./0.15 mm.

$31_p$ nmr (benzene-$d_6$): $\delta$133.7
Analysis:
Calcd for $C_{16}H_{33}NO_3P$: C, 57.8; H, 10.0; N, 8.4.
Found: C, 57.6; H, 10.0; N, 8.3.

EXAMPLE 8

3-tert-Butyl-2-(1-cyclohexyloxy-2,2,6,6-tetramethyl-piperidin-4-yloxy)-1,3,2-oxazaphospholidine The title compound is prepared according to the procedure of Example 6 from 1-cyclohexyloxy-4-hydroxy-2,2,6,6-tetramethylpiperidine (made in Example 1B). Purification of the crude product by distillation affords a 90% yield of a colorless syrup with a boiling point of 170–175° C./0.1 mm.

$31_p$ nmr (benzene-$d_6$): $\delta$134.2
Analysis:
Calcd for $C_{21}H_{41}NO_3P$: C, 63.0; H, 10.3; N, 7.0.
Found: C, 62.5; H, 10.9; N, 6.9.

EXAMPLE 9

Tris(1-alpha-methylbenzyloxy-2,2,6,6-tetramethyl-piperidin4-yl) Phosphite

A solution of 3.3 grams (24 mmol) of phosphorus trichloride in 50 ml of tetrahydrofuran is added over 20 minutes to a chilled solution (15° C.) of 20.0 grams (72.1 mmol) of 4-hydroxy-1-alpha-methylbenzyloxy-2,2,6,6-tetramethylpiperidine (made in Example 2A), 7.66 grams (75.7 mmol) of triethylamine and 200 ml of tetrahydrofuran. The reaction temperature increases to 32° C. during the addition and a white salt is formed. The reaction mixture is stirred for three hours at ambient temperature after the addition is complete. Triethylamine hydrochloride is removed by filtration, and the filtrate is concentrated at reduced pressure. Further concentration of the residue (at 100° C./0.2 mm) affords 19.4 grams (94% yield) of the title compound as a viscous oil.

$31_p$ nmr (benzene-$d_6$): $\delta$137.4
Analysis:
Calcd for $C_{51}H_{78}NO_6P$: C, 71.2; H, 9.1; N, 4.9.
Found: C, 71.0; H, 9.0; N, 4.9.

EXAMPLE 10

Tris(1-cyclohexyloxy-2,2,6,6-tetramethylpiperidin-4-yl) Phosphite

The title compound is prepared as a viscous oil in an 0% yield from 1-cyclohexyloxy-4-hydroxy-2,2,6,6-tetramethylpiperidine (prepared in Example 1B) and phosphorus trichloride according to the procedure of Example 9.

$31_p$ nmr (benzene-$d_6$) $\delta$137.6
Analysis:
Calcd for $C_{45}H_{84}NO_6P$: C, 68.1; H, 10.8; N, 5.3.
Found: C, 68.0; H, 11.0; N, 5.3.

EXAMPLE 11A

1-alpha-Methylbenzyloxy-2,2,6,6-tetramethylpiperidin-4-one

A mixture of 40.0 grams (235 mmol) of 1-oxyl-2,2,6,6-tetramethylpiperidin-4-one, 60.5 grams (470 mmol) of 70% aqueous tert-butyl hydroperoxide, 3.0 grams of molybdenum trioxide, and 200 ml of ethylbenzene is heated at reflux for four hours. Water is collected in a Dean-Stark trap. Solids are removed by filtration, and the filtrate is concentrated under reduced pressure. Kugelrohr distillation of the crude product, followed by recrystallization from methanol, affords 42.8 grams (67% yield) of the title compound as a white solid melting at 77–80° C.

EXAMPLE 11B

1-Dodecylamino-1-alpha-methylbenzyloxy-2,2,6,6-tetramethylpiperidine

A solution of 11.1 grams (185 mmol) of acetic acid in 40 ml of tetrahydrofuran is added dropwise to a mixture of 10.0 grams (36.3 mmol) of 1-alpha-methylbenzyloxy2,2,6,6-tetramethylpiperidin-4-one, 26.9 grams (145 mmol) of dodecylamine, 80 ml of tetrahydrofuran, and 5A molecular sieves. The reaction mixture is cooled below 25° C., and 2.51 grams (40 mmol) of sodium cyanoborohydride is added over five minutes. The reaction mixture is stirred at ambient temperature for three hours after the addition is complete. Solids are removed by filtration, and the filtrate is evaporated to an oil which is then dissolved in ether (200 ml). The ether solution is washed with cold 5% sodium hydroxide solution (200 ml), washed with saturated sodium chloride solution, dried over anhydrous magnesium sulfate and concentrated at reduced pressure. Purification of the crude product by flash chromatography affords 13.1 grams (81% yield) of the title compound as a colorless oil.

Analysis:
Calcd for $C_{29}H_{52}N_2O$: C, 78.3; H, 11.8; N, 6.3.
Found: C, 77.7; H, 11.6; N, 6.6.

EXAMPLE 11C 5,5-Dimethyl-2-[N-(1-alpha-methylbenzyloxy-2,2,6,6-tetra-methylpiperidin-4-yl)
-N-dodecylamino]-1,3,2-dioxaphosphorinane A solution of 3.03 grams (18.0 mmol) of 2-chloro-5,5-dimethyl-1,3,2-dioxaphosphorinane in 10 ml of tetrahydrofuran is added over ten minutes to a solution of 8.00 grams (18.0 mmol) of 4-dodecylamino-1-alpha-methyl-benzyloxy2,2,6,6-tetramethylpiperidine, 1.91 grams (18.9 mmol) of triethylamine, and 25 ml of tetrahydrofuran. The reaction temperature increases from 20° C. to 30° C. during the addition, and triethylamine hydrochloride precipitates from solution. The reaction mixture is stirred at ambient temperature for two hours. The precipitate is removed by filtration, and the filtrate is concentrated at reduced pressure. Residual volatiles are removed by Kugelrohr distillation (at 100° C./0.2 mm) to afford 10.1 grams (97% yield) of the title compound as a viscous oil.

$31_p$ nmr (benzene-$d_6$):$\delta$147.9
Analysis:
Calcd for $C_{34}H_{61}N_2O_3P$: C, 70.8; H, 10.7; N, 4.9.
Found: C, 70.8; H, 10.6; N, 5.0.

EXAMPLE 12A

1-Cyclohexyloxy-4-dodecylamino-2,2,6,6-tetramethylpiperidine

The title compound is prepared in 82% yield as a colorless syrup from 1-cyclohexyloxy-2,2,6,6,-tetramethyl-piperidin-4-one and dodecylamine according to the procedure of Example 11B.

Analysis:
Calcd for $C_{27}H_{54}N_2O$: C, 76.7; H, 12.9; N, 6.6.
Found: C, 76.7; H, 13.2; N, 6.7.

EXAMPLE 12B

2-[N(1-Cyclohexyloxy-2,2,6,6-tetramethylpiperidin-4-yl)-N-dodecylamino]
-5,5-dimethyl-1,3,2-dioxaphosphorinane The title compound is a yellow syrup prepared from 1-cyclohexyloxy-4-dodecylamino-2,2,6,6-tetramethyl-piperidine and 2-chloro-5,5-dimethyl-1,3,2-dioxaphosphorinane according to the procedure of Example 11C.

$31_p$ nmr (benzene-$d_6$): $\delta$146.8
Analysis:
Calcd for $C_{32}H_{63}N_2O_3P$: C, 69.3; H, 11.4; N, 5.0.
Found: C, 66.6; H, 11.0; N, 5.0.

EXAMPLE 13A 4-n-Butylamino-1-alpha-methylbenzyloxy-2,2,6,6-tetramethylpiperidine The title compound is prepared in 74% yield as a colorless syrup from n-butylamine and 1-alpha-methylbenzyloxy-2, 2,6,6-tetramethylpiperidin-4-one (made in Example 11A) according to the procedure of Example 11B. Acetonitrile is substituted for tetrahydrofuran as the reaction solvent and toluene is substituted for ether in the isolation steps.

Analysis:
Calcd for $C_{21}H_{36}N_2O$: C, 75.8; H, 10.9; N, 8.4.
Found: C, 74.7; H, 11.0; N, 8.6.

EXAMPLE 13B

2-[N-(1-alpha-Methylbenzyloxy-2,2,6,6-tetramethyl-piperidin-4-yl)-N-n-butylamino]
-5,5-dimethyl-1,3,2-dioxaphosphorinane The title compound is prepared as a colorless glass from 4-n-butylamino-1-alpha-methylbenzyloxy-2,2,6,6-tetramethylpiperidine and 2-chloro-5,5-dimethyl-1,3,2-dioxaphosphorinane according to the procedure of Example 11C.

$31_p$ nmr (benzene-$d_6$): $\delta$147.9
Analysis:
Calcd for $C_{26}H_{45}N_2O_3P$: C, 67.2; H, 9.8; N, 6.0.
Found: C, 66.8; H, 9.5; N, 5.8.

EXAMPLE 14

3,9-Bis[(N-(1-alpha-methylbenzyloxy-2,2,6,6-tetramethyl-piperidin-4-yl))-dodecylamino]-2,
4,8,10-tetraoxa-3,9-diphosphaspiro[5.5]undecane A solution of 8.2 grams (18.4 mmol) of 4-dodecylamino 1-alpha-methylbenzyloxy-2,2,6,6-tetramethylpiperidine (made in Example 11B), 1.86 gram (18.4 mmol) of triethylamine, and 30 ml of tetrahydrofuran is added dropwise over a fifteen minute period to a solution of 2.44 grams (9.2 mmol) of 3,9-dichloro 2,4,8,10-tetraoxa-3,9-diphosphaspiro[5.5]undecane in 20 ml of tetrahydrofuran. The reaction mixture is then stirred at ambient temperature for four hours. Triethylamine hydrochloride is removed by filtration, and the filtrate is evaporated at reduced pressure to afford 9.88 grams of the title compound as a colorless syrup.

$31_p$ nmr (benzene-$d_6$): $\delta$146.4
Analysis:
Calcd for- $C_{63}H_{110}N_4O_6P_2$:C, 70.0; H, 10.3; N, 5.2.
Found: C, 70.1; H, 10.3; N, 5.4.

EXAMPLE 15

3,9-Bis-[(N-(1-cyclohexyloxy-2,2,6,6-tetramethyl-piperidin4-yl))-dodecylamino]-2,
4,8,10-tetraoxa-3,9-diphosphaspiro[5.5]undecane The title compound is prepared as a viscous oil from 1-cyclohexyloxy-4-dodecylamino-2,2,6,6-tetramethyl-piperidine (made in Example 12A) and 3,9-dichloro-2,4,8,10-tetraoxa-3, 9-diphosphaspiro-[5.5]undecane according to the procedure of Example 14.

$31_p$ nmr (benzene-$d_6$): $\delta$148.4
Analysis:
Calcd for $C_{59}H_{114}N_4O_6P_2$ C, 68.3; H, 11.1; N, 5.4.
Found: C, 65.7; H, 11.0; N, 5.4.

EXAMPLE 16

3,9-Bis[(N-(1-alpha-methylbenzyloxy-2,2,6,6-tetramethyl-yl-piperidin-4- yl))-n-butylamino]-2,
4,8,10-tetraoxa-3,9-diphosphaspiro[5.5]undecane The title compound is prepared as a viscous syrup from 4-n-butylamino-1-alpha-methylbenzyloxy-2,2,6,6-tetramethylpiperidine (made in Example 13A) and 3,9-dichloro-2,4,8,10-tetraoxa-3, 9-diphosphaspiro[5.5]undecane according to the procedure of Example 14.

$31_p$ (benzene-d$_6$): δ148.4
Analysis:
Calcd for C$_{47}$H$_{78}$N$_4$O$_6$P$_2$: C, 65.9; H, 9.2; N, 6.5.
Found: C, 65.5; H, 8.8; N, 6.3.

EXAMPLE 17A 4-n-Butylamino-1-cyclohexyloxy-2,2,6,6-tetramethylpiperidine

A mixture of 9.5 grams (37.5 mmol) of 1-cyclohexyloxy-2, 2,6,6-tetramethylpiperidin-4-one, 13.7 grams (187 mmol) of n-butylamine, 0.4 gram of platinum oxide, and 120 ml of ethanol is hydrogenated on a Parr apparatus (50 psi, ambient temperature) till hydrogen uptake ceases. The catalyst is removed by filtration and the filtrate is evaporated to afford 10.8 grams (93% yield) of the title compound as a colorless syrup.
Analysis:
Calcd for C$_{19}$H$_{38}$N$_2$O: C, 73.5; H, 12.3; N, 9.0.
Found: C, 73.0; H, 12.6; N, 8.6.

EXAMPLE 17B 3,9-Bis[(N-(1-cyclohexyloxy-2,2,6,6-tetramethyl-piperidin4-yl))-n-butylamino]-2, 4,8,10-tetraoxa-3,9-diphosphaspiro[5.5]undecane The title compound is prepared as a colorless glass from 4-n-butylamino-1-cyclohexyloxy-2,2,6,6-tetramethylpiperidine and 3,9-dichloro-2,4,8,10-tetraoxa-3,9-diphosphaspiro5.5]undecane according to the procedure of Example 14.
$31_p$ nmr (benzene-d$_6$): δ148.4
Analysis:
Calcd for C$_{43}$H$_{82}$N$_4$O$_6$P$_2$ C, 63.5; H, 10.2; N, 6.9.
Found: C, 59.7; H, 9.9; N, 6.1.

EXAMPLE 18

3-tert-Butyl-2-[bis(1-cyclohexyloxy-2,2,6,6-tetramethyl-piperidin4-yl)] amino-1,3,2-oxazapholidine The title compound is prepared from bis(1-cyclohexyloxy-2, 2 6,6-tetramethylpiperidin-4-yl)amine and 3-tert-butyl-2-chloro-1, 3,2-oxazapholidine according to the procedure of Example 6.

EXAMPLE 19

3,9-Bis[bis(1-cyclohexyloxy-2,2,6,6-tetramethylpiperidin-4yl)amino]-2, 4,8,10-tetraoxa-3,9-diphosphaspiro[5.5]undecane The title compound is prepared from bis(1-cyclohexyloxy-2,2,6,6-tetramethylpiperidin-4-yl)amine and 3,9-dichloro-2,4,8,10-tetraoxa-3,9-diphosphaspiro[5.5]undecane according to the procedure of Example 14.

EXAMPLE 20

N,N'-Bis(5,5-dimethyl-1,3,2-dioxaphosphorinan-2-yl)-N,N'bis(1-cyclohexyloxy-2, 2,6,6-tetramethylpiperidin-4-yl)hexamethylenediamine The title compound is prepared from N,N'-bis(1-cyclohexyloxy-2, 2,6,6-tetramethylpiperidin-4-yl)hexamethylenediamine and 2-chloro-5,5-dimethyl-1,3,2-dioxaphosphorinane according to the procedure of Example 11C.

EXAMPLE 21

N,N'-Bis(1,3,2-dioxaphospholan-2-yl)-N,N'-bis(1-methoxy2, 2,6,6-tetramethylpiperidin-4-yl)hexamethylenediamine The title compound is prepared from N,N'-bis(1-methoxy2, 2,6,6-tetramethylpiperidin-4-yl)hexamethylenediamine and 2-chloro-3,2-dioxaphospholane according to the procedure of Example 11C.

EXAMPLE 22

2,4,8,10-Tetra-tert-butyl-6-(1-methoxy-2,2,6,6-tetramethylpiperidin-4-yloxy) dibenzo[d,f][1,3,2]dioxaphosphepin The title compound is prepared from 4-hydroxy-1-methoxy-2, 2,6,6-tetramethylpiperidine and 2,4,8,10-tetra-tert-butyl-6-chlorodibenzo [d,f][1,3,2]dioxaphosphepin according to the procedure of Example 1C.

EXAMPLE 23

1,3-Dimethyl-2-(1-octyloxy-2,2,6,6-tetramethylpiperidin-4-yloxy)-1, 3,2-diazaphospholidine The title compound is prepared from 4-hydroxy-1-octyloxy-2, 2,6,6-tetramethylpiperidine and 2-chloro-1,3-dimethyl-1,3,2-diazaphospholidine according to the procedure of Example 6.

EXAMPLE 24

1,3-Bis(1-cyclohexyloxy-2,2,6,6-tetramethylpiperidin-4-yl)--(1-cyclohexyloxy-2,2,6,6-tetramethylpiperidin-4-yloxy)1,3,2-diazaphospholidine The title compound is prepared from 1,3-bis(1- cyclohexyloxy-2,2,6,-tetramethylpiperidin-4-yl)-2-chloro1,3,2-diazaphospholidine and 1-cyclohexyloxy-4-hydroxy2,2,6,6-tetramethylpiperidine according to the procedure of Example 6.

EXAMPLE 25

Light Stabilization of Polypropylene

This example illustrates the light stabilizing effectiveness of the instant stabilizers.

Poypropylene powder (Himont Profax 6501) stabilized with 0.% by weight of n-octadecyl 3,5-di-tert-butyl4-hydroxyhydrocinnamate and containing 0.1% by weight of calcium stearate is thoroughly blended with 0.1% by weight of the :est additive. The blended materials are then milled on a two-roll mill at 182° C for five minutes, after which time the stabilized polypropylene is sheeted from the mill and allowed to cool. The milled polypropylene is then cut into pieces and compression molded on a hydraulic press at 250° C and 175 psi; (1.2 x 106 Pa) into 5 mil (0.127 mm) films. The sample :s exposed in a fluorescent sunlight/black light chamber until failure. Failure is taken as the :ours required to reach 0.5 carbonyl absorbance by infrared spectroscopy on the exposed films.

| Additive Compound of Example | FS/BL Test Results (hours to failure) |
| --- | --- |
| Control* | 420 |
| 1C | 670 |
| 8 | 1290 |
| 17B | 1020 |
| 7 | 1230 |
| 10 | 1640 |

-continued

| Additive Compound of Example | FS/BL Test Results (hours to failure) |
|---|---|
| 16 | 930 |
| 6 | 940 |
| 9 | 1010 |
| 11C | 880 |
| 12B | 1390 |
| 14 | 890 |
| 15 | 1270 |

*Control is the polypropylene containing only calcium stearate and octadecyl 3,5-di-tert-butyl-4-hydroxyhydrocinnamate.

EXAMPLE 26
Stabilization of a Flexible High Solids Thermoset Acrylic Resin Enamel A thermoset acrylic enamel based on a binder made from 2-hydroxyethyl acrylate, butyl acrylate, methyl methacrylate, styrene and acrylic acid and modified with a polyester urethane and with a melamine resin and an acid catalyst is formulated to include a 2H-benzotriazole UV abseorber and a hindered amine light stabilizer.

Commercially available epoxy resin primed 4 in×12 in 10.16 cm×30.48 cm) panels (Uniprime from Advanced Coatings Technology,) are spray coated with a silver metallic basecoat to a thickness of about 0.8 mil (0.023 mm) and air dried for three minutes. Prior to application, the basecoat is stabilized with 1% (by weight) each of 2-(2-hydroxy-3,5-di-tert-amylphenyl)-2H-benzotriazole and of bis(3,5-di-tert-butyl-4-hydroxybenzyl) 2-butyl-2(1,2,2,6,6-pentamethylpiperidin-ylmalonate based on the solid resin. The stabilized thermoset acrylic resin enamel is then sprayed onto the basecoated panel to a thickness of about 2 mil (0.05 mm). After air drying for fifteen minutes, the coated sheets are baked for 30 minutes at 250° F. (121° C.).

After storage for 1 week in a air-conditioned room, the coated panels are subjected to weathering in a QUV exposure apparaturs according to test method ASTM G-53/77. In this test, the samples are subjected to weathering in repeated cycles for 4 hours in a humid atmosphere at 50° C. and then for 8 hours under UV light at 70° C. The 20° gloss values of the panels are determined at various intervals as reported in the table below.

| Additive* (% by weight) | 20° Gloss After QUV Exposure (Hours) | | | | | |
|---|---|---|---|---|---|---|
| | 0 | 339 | 646 | 978 | 1297 | 1608 |
| Unstabilized enamel | 90 | 84 | 76 | 1** | — | — |
| 2% UVA plus 2% Compound of Example 1C | 92 | 90 | 89 | 84 | 68 | 13 |

*UVA is 2-[2-hydroxy-3-tert-butyl-5-(2-omega-hydroxy-octa(ethylene-oxy)carbonyl)-ethylphenyl]-2H-benzotriazole
**Cracking is observed.

EXAMPLE 27
Stabilization of a Medium Oil Alkyd Enamel

A commercially available medium oil alkyd enamel pigmented with non-leafing aluminum pigment and tinted light blue is stabilized with 3% by weight of a 2H-benzotriazole UV absorber and an instant compound. The stabilized enamel is then spray applied onto cold rolled steel panels primed with an epoxy primer (as described in Example 26). After the coating is allowed to cure at room temperature for two weeks, the panels are exposed outdoors at an angle of 5° south. The 60° gloss values of the panels are determined during exposure as seen in the table below.

| Additive* (% by weight) | 60° Gloss After Outdoor Exposure (in Months) | | | | | | |
|---|---|---|---|---|---|---|---|
| | 0 | 2 | 6 | 8 | 10 | 12 | 14 |
| Unstabilized Alkyd Enamel | 95 | 74 | 32 | 19 | 13 | 6 | 6 |
| 3% UVA plus 2% Compound of Example 8 | 95 | 88 | 72 | 69 | 62 | 54 | 37 |

*UVA is 2-[2-hydroxy-3-tert-butyl-5-(2-omega-hydroxy-octa-(ethyleneoxy)carbonyl)-ethylphenyl]-2H-benzotriazole

EXAMPLE 28

A white PVC plastisol coil coating is stabilized with the indicated amounts of UV absorber and instant stabilizer (% by weight based on the total resin solids). The additives are first dissolved in an aromatic solvent, then incorporated into the resin using a high speed disperser. The coatings are deaerated before application.

Application is by an 8 mil gap square drawdown bar over a phenolic primer on 4 inch×12 inch (10.16 cm×30.48 cm) galvanized steel panels to dry to a film thickness of 2.5-3.5 mils. The coatings are baked at an oven temperature of 550° F. (288° C.) for 80 seconds to a peak metal temperature of 400° F. (204° C.), then quenched in cold water. The coated panels are weathered in a QUV exposure apparatus for 1944 hours using 340A bulbs and a cycle of 8 hours UV light at 60° C. alternating with 4 hours of darkness (condensing humidity) at 50° C.

| Stabilizer* | 60° Gloss Retention (in %) After 1944 Hours Exposure in the QUV | Delta Yellowness Index (YI) After 1944 Hours Exposure in the QUV |
|---|---|---|
| None | 40 | 9.38 |
| 2% UVA | 44 | 9.29 |
| 2% UVA plus 2% Compound of Example 1C | 84 | 4.16 |
| 2% UVA plus 2% Compound of Example 8 | 82 | 4.55 |
| 2% UVA plus 2% Compound of Example 7 | 84 | 2.69 |
| 2% UVA plus 2% Compound of Example 17B | 67 | 3.65 |
| 2% UVA plus 2% Compound of Example 12B | 89 | 3.90 |
| 2% UVA plus 2% Compound of Example 10 | 70 | 3.43 |

*UVA is 2-[2-hydroxy-3-tert-butyl-5-(2-omega-hydroxy-octa-(ethyleneoxy)carbonyl)-ethylphenyl]-2H-benzotriazole.

What is claimed is:

1. A compound which is an N-hydrocarbyloxy hindered amine substituted by a trivalent phosphorus moiety having a formula I, II, II, IV or V

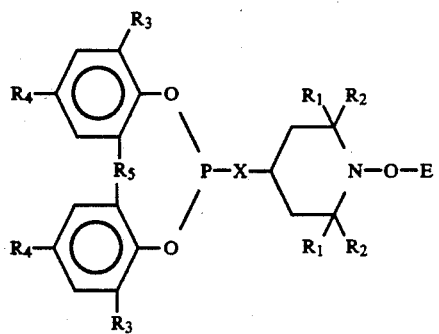 (I)

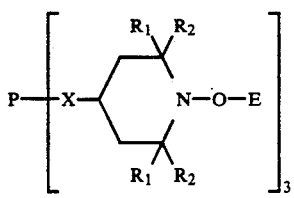 (II)

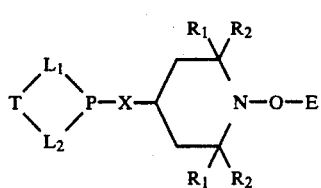 (III)

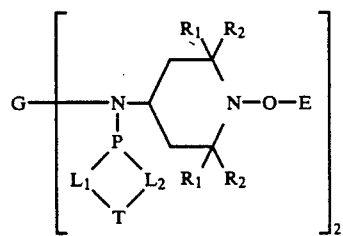 (IV)

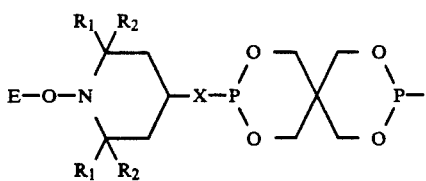 (V)

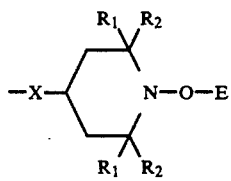

wherein
   $R_1$ and $R_2$ are independently methyl or ethyl or $R_1$ and $R_2$ together are pentamethylene,
   $R_3$ and $R_4$ are independently alkyl of 1 to 4 carbon atoms,
   $R_5$ is a direct bond, methylene or 1,1-alkylidene of 2 to 5 carbon atoms,
   X is —O— or —NY— where Y is hydrogen or alkyl of 1 to 18 carbon atoms, or X is

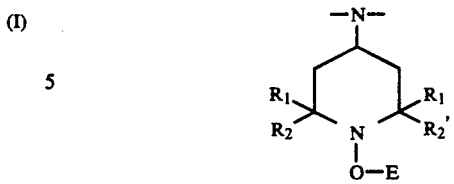

$L_1$ and $L_2$ are independently —O— or —NY— where Y is hydrogen or alkyl of 1 to 18 carbon atoms, or $L_1$ and $L_2$ are independently

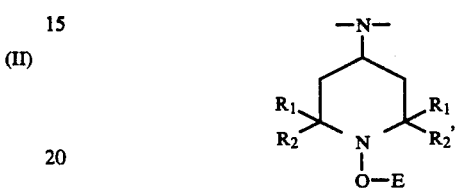

T is alkylene of 2 or 3 carbon atoms or said alkylene substituted by one or two alkyl groups each of 1 to 4 carbon atoms,
G is alkylene of 2 to 12 carbon atoms, and
E is alkyl of 1 to 18 carton atoms, cycloalkyl of 5 to 12 carbon atoms, alkenyl of 2 to 8 carbon atoms, cycloalkenyl of 5 to 12 carbon atoms, aralkyl of 7 to 15 carbon atoms, a radical of a saturated or unsaturated bicyclic or tricyclic hydrocarbon of 7 to 12 carbon atoms or aryl of 6 to 10 carbon atoms or said aryl substituted by alkyl.

2. A compound according to claim 1 wherein $R_1$ and $R_2$ are each methyl.

3. A compound according to claim 1 wherein $R_3$ and $R_4$ are independently methyl or tert-butyl.

4. A compound according to claim 3 wherein $R_3$ and $R_4$ are each tert-butyl.

5. A compound according to claim 1 wherein $R_5$ is a direct bond or methylene.

6. A compound according to claim 5 wherein $R_5$ is methylene.

7. A compound according to claim 1 wherein X is —O— or —NY— where Y is n-butyl or dodecyl, or X is

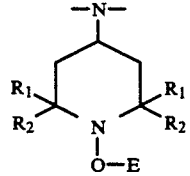

where $R_1$ and $R_2$ are each methyl.

8. A compound according to claim 1 wherein $L_1$ and $L_2$ are independently —O— or —NY— where Y is tert-butyl.

9. A compound according to claim 8 wherein $L_1$ and $L_2$ are each —O— or one of $L_1$ and $L_2$ is —O— and the other is —NY— where Y is tert-butyl.

10. A compound according to claim 1 wherein T is ethylene or 2,2-dimethyltrimethylene.

11. A compound according to claim 1 wherein G is hexamethylene.

12. A compound according to claim 1 wherein E is alkyl of 1 to 9 carbon atoms, cyclohexyl or alpha-methylbenzyl.

13. A compound according to claim 12 wherein E is methyl, heptyl, octyl, cyclohexyl or alpha-methylbenzyl.

14. The compound according to claim 1 which is 2,4,8,10-tetra-tert-butyl-6-(1-cyclohexyloxy-2,2,6,6-tetra-methylpiperidin-4-yloxy) -12H-dibenzo[d,g][1,3,2]dioxaphosphocin.

15. The compound according to claim 1 which is 2,4,8,10-tetra-tert-butyl-6-(1-alpha-methylbenzyloxy2,2,6,6-tetramethylpiperidin -4-yloxy)-12H-dibenzo[d,g][1,3,2]dioxaphosphocin.

16. The compound according to claim 1 which is 2,4,8,10-tetra-tert-butyl-6-(1-ethoxy-2,2,6,6-tetramethyl-piperidin-4-yloxy]-12H-dibenzo [d,g][1,3,2]dioxaphosphocin.

17. The compound according to claim 1 which is 2,4,8,10-tetra-tert-butyl-6-(1-benzyloxy-2,2,6,6-tetramethylpiperidin-4-yloxy)-12H-dibenzo [d,g][1,3,2]dioxaphosphocin.

18. The compound according to claim 1 which is 2,4,8,10-tetra-tert-butyl-6-(1-methoxy-2,2,6,6-tetramethyl-piperidin-4-yl)-12H-dibenzo [d,g][1,3,2]dioxaphosphocin.

19. The compound according to claim 1 which is 3-tert-butyl-2-(1-alpha-methylbenzyloxy-2,2,6,6-tetramethylpiperidin-4-yloxy) -1,3,2-oxazapholidine.

20. The compound according to claim 1 which is 3-tert-butyl-2-(1-methoxy-2,2,6,6-tetramethylpiperidin-4-yloxy)-1,3,2-oxazapholidine.

21. The compound according to claim 1 which is 3-tert-butyl-2-(1-cyclohexyloxy-2,2,6,6-tetramethyl-piperidin-4-yloxy)-,1,3,2-oxazapholidine.

22. The compound according to claim 1 which is tris(1-alpha-methylbenzyloxy-2,2,6,6-tetramethylpiperidin-4-yl) phosphite.

23. The compound according to claim 1 which is tris(1-cyclohexyloxy-2,2,6,6-tetramethylpiperidin-4-yl) phosphite.

24. The compound according to claim 1 which is 5,5-dimethyl-2-[N-(1-alpha-methylbenzyloxy-2,2,6,6-tetra-methylpiperidin-4-yl) -N-dodecylamino]-1,3,2-dioxaphosphorinane.

25. The compound according to claim 1 which is 2-[N-(1-cyclohexyloxy-2,2,6,6-tetramethylpiperidin-4-yl)-N-dodecylamino] -5,5-dimethyl-1,3,2-dioxaphosphorinane.

26. The compound according to claim 1 which is 2-[N-(1-alpha-methylbenzyloxy-2,2,6,6-tetramethyl-piperidin-4-yl)-N-n-butylamino]-5, 5-dimethyl-1,3,2-dioxaphosphorinane.

27. The compound according to claim 1 which is 3,9-bis[(N-1-alpha-methylbenzyloxy-2,2,6,6-tetramethyl-piperidin-4-yl))-dodecylamino]-2, 4,8,10-tetraoxa-3,9-diphosphoaspiro[5.5]undecane.

28. The compound according to claim 1 which is 3,9-bis[(N-(1-cyclohexyloxy-2,2,6,6-tetramethylpiperidin-4-yl))-dodecylamino]-2, 4,8,10-tetraoxas-3,9-diphosphaspiro[5.5]undecane.

29. The compound according to claim 1 which is 3,9-bis[(n-(1-alpha-methylbenzyloxy)-2,2,6,6-tetra-methylpiperidin-4-yl))-n-butylamino]-2, 4,8,10-tetraoxa-3,9-diphosphaspiro[5.5]undecane.

30. The compound according to claim 1 which is 3,9-bis[(N-(1-cyclohexyloxy-2,2,6,6-tetramethylpiperidin-4-yl))-n-butylamino]-2, 4,8,10-tetraoxa-3,9-diphosphaspiro[5,5]undecane.

31. A composition stabilized against the deleterious effects of actinic light which comprises
(a) a polymer subject to degradation caused by the deleterious effects of actinic light, and
(b) a stabilizing amount of a compound according to claim 1.

32. A composition according to claim 31 wherein the polymer is a polyolefin.

33. A composition according to claim 32 wherein the polyolefin is polypropylene.

34. A composition according to claim 31 wherein the compound of component (b) is tris(1-cyclohexyloxy-2,2,6,6-tetramethylpiperidin-4-yl) phosphite.

35. A composition according to claim 31 wherein the polymer is a thermoset acrylic resin or an alkyd enamel.

36. A composition according to claim 31 wherein the polymer is a coating system based on alkyd, acrylic, acrylic-alkyd, polyester, epoxide, urethane, polyamide, vinyl or epoxy-polyester resins.

37. A composition according to claim 31 wherein the compound of component (b) is
2,4,8,10-tetra-tert-butyl-6-(1-cyclohexyloxy-2,2,6,6-tetra-methylpiperidin-4-yloxy) -12H-dibenzo[d,g][1,3,2]dioxaphosphocin;
3-tert-butyl-2-(1-methoxy-2,2,6,6-tetramethylpiperidin-4-yloxy)-1,3,2-oxazapholidine;
3-tert-butyl-2-(1-cyclohexyloxy-2,2,6,6-tetramethyl-piperidin-4-yloxy)-1,3,2-oxazapholidine;
2-[N-(1-cyclohexyloxy-2,2,6,6-tetramethylpiperidin-4-yl)-N-dodecylamino]-5, 5-dimethyl-1,3,2-dioxaphosphorinane;
3,9-bus[(N-(1-cyclohexyloxy-2,2,6,6-tetramethyl-piperidin-4-yl))-dodecylamino]-2, 4,8,10-tetraoxas-3,9-diphosphaspiro[5.5]undecane; or
3,9-bis[(N-(1-cynexyloxy-2,2,6,6-tetramethyl-piperidin-4-yl))-n-butylamino]-2, 4,8,10-tetraoxa-3,9-diphosphaspiro[5,5]undecane.

38. A composition according to claim 36 which contains a UV absorber or additional light stabilizer.

39. A method for stabilizing a synthetic polymer against oxidative, thermal or actinic degradation which comprises incorporation into said synthetic polymer an effective stabilizing amount of a compound according to claim 1.

* * * * *